US011432868B2

United States Patent
Price et al.

(10) Patent No.: US 11,432,868 B2
(45) Date of Patent: *Sep. 6, 2022

(54) ULTRASONIC SURGICAL INSTRUMENT WITH ELECTROSURGICAL FEATURE

(71) Applicant: Cilag GmbH International, Zug (CH)

(72) Inventors: Daniel W. Price, Loveland, OH (US); Benjamin D. Dickerson, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 758 days.

This patent is subject to a terminal disclaimer.

(21) Appl. No.: 15/910,271

(22) Filed: Mar. 2, 2018

(65) Prior Publication Data
US 2018/0256245 A1   Sep. 13, 2018

Related U.S. Application Data

(63) Continuation of application No. 14/086,085, filed on Nov. 21, 2013, now Pat. No. 9,949,785.

(51) Int. Cl.
*A61B 18/18* (2006.01)
*A61B 18/14* (2006.01)
(Continued)

(52) U.S. Cl.
CPC ...... *A61B 18/1445* (2013.01); *A61B 2017/00022* (2013.01); *A61B 2017/00026* (2013.01);
(Continued)

(58) Field of Classification Search
CPC ...... A61B 18/1445; A61B 2017/00022; A61B 2017/00026; A61B 2017/00039;
(Continued)

(56) References Cited

U.S. PATENT DOCUMENTS 4,903,696 A * 2/1990 Stasz ................. A61B 18/1206
606/37
5,322,055 A 6/1994 Davison et al.
(Continued)

FOREIGN PATENT DOCUMENTS

CN 102497827 A 6/2012
CN 102639075 A 8/2012
(Continued)

OTHER PUBLICATIONS

U.S. Appl. No. 13/657,553, filed Oct. 22, 2012.
(Continued)

*Primary Examiner* — Michael F Peffley
*Assistant Examiner* — Amanda L Zink
(74) *Attorney, Agent, or Firm* — Frost Brown Todd LLC

(57) ABSTRACT

A surgical instrument system includes an end effector, a generator, and a controller. The end effector includes an ultrasonic blade and at least one electrode surface. The generator provides power to the end effector. The end effector applies ultrasonic energy to tissue via the blade or RF energy to tissue via the at least one electrode surface. The controller is configured to select between one or both of ultrasonic energy or RF energy, and thereby control the generator to provide the selected one or both of ultrasonic energy or RF energy at the end effector, based on a sensed operating condition of the end effector. The controller may select between ultrasonic energy and RF energy based on whether a clamp arm is in an open position relative to the blade, based on which button is being activated, and based on whether tissue is sensed at the end effector.

18 Claims, 12 Drawing Sheets

(51) Int. Cl.
　　　*A61B 18/00*　　　(2006.01)
　　　*A61B 17/32*　　　(2006.01)
　　　*A61B 90/00*　　　(2016.01)
　　　*A61B 17/00*　　　(2006.01)
(52) U.S. Cl.
　　　CPC .............. *A61B 2017/00039* (2013.01); *A61B 2017/320069* (2017.08); *A61B 2017/320071* (2017.08); *A61B 2017/320089* (2017.08); *A61B 2017/320094* (2017.08); *A61B 2017/320095* (2017.08); *A61B 2018/00642* (2013.01); *A61B 2018/00875* (2013.01); *A61B 2090/064* (2016.02); *A61B 2090/067* (2016.02)
(58) Field of Classification Search
　　　CPC ....... A61B 2017/320069; A61B 2017/320071; A61B 2017/320089; A61B 2017/320094; A61B 2017/320095; A61B 2018/00642; A61B 2018/00875; A61B 2090/064; A61B 2090/067
　　　See application file for complete search history.

(56) References Cited

U.S. PATENT DOCUMENTS

| | | | |
|---|---|---|---|
| 5,873,873 A | 2/1999 | Smith et al. | |
| 5,980,510 A | 11/1999 | Tsonton et al. | |
| 6,056,735 A * | 5/2000 | Okada | A61B 17/320092 606/1 |
| 6,325,811 B1 | 12/2001 | Messerly | |
| 6,454,781 B1 * | 9/2002 | Witt | A61B 17/320092 606/169 |
| 6,500,176 B1 | 12/2002 | Truckai et al. | |
| 6,562,032 B1 * | 5/2003 | Ellman | A61B 17/320068 606/41 |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 8,292,888 B2 * | 10/2012 | Whitman | A61N 7/02 606/51 |
| 8,461,744 B2 | 6/2013 | Wiener et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,161,803 B2 | 10/2015 | Yates et al. | |
| 9,381,058 B2 | 7/2016 | Houser et al. | |
| 9,393,037 B2 | 7/2016 | Olson et al. | |
| 9,949,785 B2 | 4/2018 | Price et al. | |
| 2003/0018331 A1 * | 1/2003 | Dycus | A61B 18/085 606/48 |
| 2006/0079874 A1 | 4/2006 | Faller et al. | |
| 2007/0191713 A1 | 8/2007 | Eichmann et al. | |
| 2007/0191828 A1 * | 8/2007 | Houser | A61B 17/320092 606/40 |
| 2007/0282333 A1 | 12/2007 | Fortson et al. | |
| 2008/0132887 A1 * | 6/2008 | Masuda | A61B 18/1445 606/37 |
| 2008/0200940 A1 | 8/2008 | Eichmann et al. | |
| 2009/0254080 A1 * | 10/2009 | Honda | A61B 18/1402 606/38 |
| 2010/0069940 A1 | 3/2010 | Miller et al. | |
| 2010/0268206 A1 * | 10/2010 | Manwaring | A61B 17/00234 606/29 |
| 2011/0087212 A1 | 4/2011 | Aldridge et al. | |
| 2012/0112687 A1 | 5/2012 | Houser et al. | |
| 2012/0116265 A1 | 5/2012 | Houser et al. | |
| 2012/0265196 A1 * | 10/2012 | Turner | H03M 11/24 606/34 |
| 2013/0190660 A1 | 7/2013 | Tanaka et al. | |
| 2014/0005681 A1 * | 1/2014 | Gee | A61F 9/00745 606/130 |
| 2014/0005701 A1 * | 1/2014 | Olson | A61B 17/320092 606/169 |
| 2014/0018802 A1 * | 1/2014 | Whitman | A61B 18/1442 606/48 |
| 2014/0114327 A1 * | 4/2014 | Boudreaux | A61B 90/06 606/130 |
| 2014/0135804 A1 * | 5/2014 | Weisenburgh, II | A61B 17/29 606/169 |

FOREIGN PATENT DOCUMENTS

| | | | |
|---|---|---|---|
| CN | 103027748 A | | 4/2013 |
| EP | 2111813 A1 | | 10/2009 |
| EP | 2484301 A1 | | 8/2012 |
| JP | H05-212048 A | | 8/1993 |
| JP | 2009-261943 A | | 11/2009 |
| JP | 2011-087937 A | | 5/2011 |
| JP | 2012-120881 A | | 6/2012 |
| JP | 2015-513433 A | | 5/2015 |
| JP | 2015-514474 A | | 5/2015 |
| WO | WO 2005/122918 A1 | | 12/2005 |
| WO | WO 2011/099571 A1 | | 8/2011 |
| WO | WO 2012/135705 A1 | | 10/2012 |
| WO | WO 2013/141218 A1 | | 9/2013 |

OTHER PUBLICATIONS

U.S. Appl. No. 61/410,603, filed Nov. 5, 2010.
International Search Report and Written Opinion dated Feb. 6, 2015 for International Application No. PCT/US2014/065426, 10 pages.
Chinese Office Action, The First Office Action, and First Search, dated Jan. 29, 2018 for Application No. CN 201480063408.1, 12 pgs.
European Examination Report dated Dec. 4, 2019 for Application No. EP 14812334.2, 5 pgs.
Japanese Office Action, Notice of Reasons for Refusal, and First Search, dated Sep. 11, 2018 for Application No. JP 2016-533131, 19 pgs.
Brazil Office Action dated Mar. 11, 2020, for Application No. BR112016011384-5, 4 pages.
Extended European Search Report dated Apr. 15, 2021, for Application No. 20214327.7, 7 pages.
Indian Office Action dated Mar. 16, 2020, for Application No. 201617018503, 7 pages.

* cited by examiner

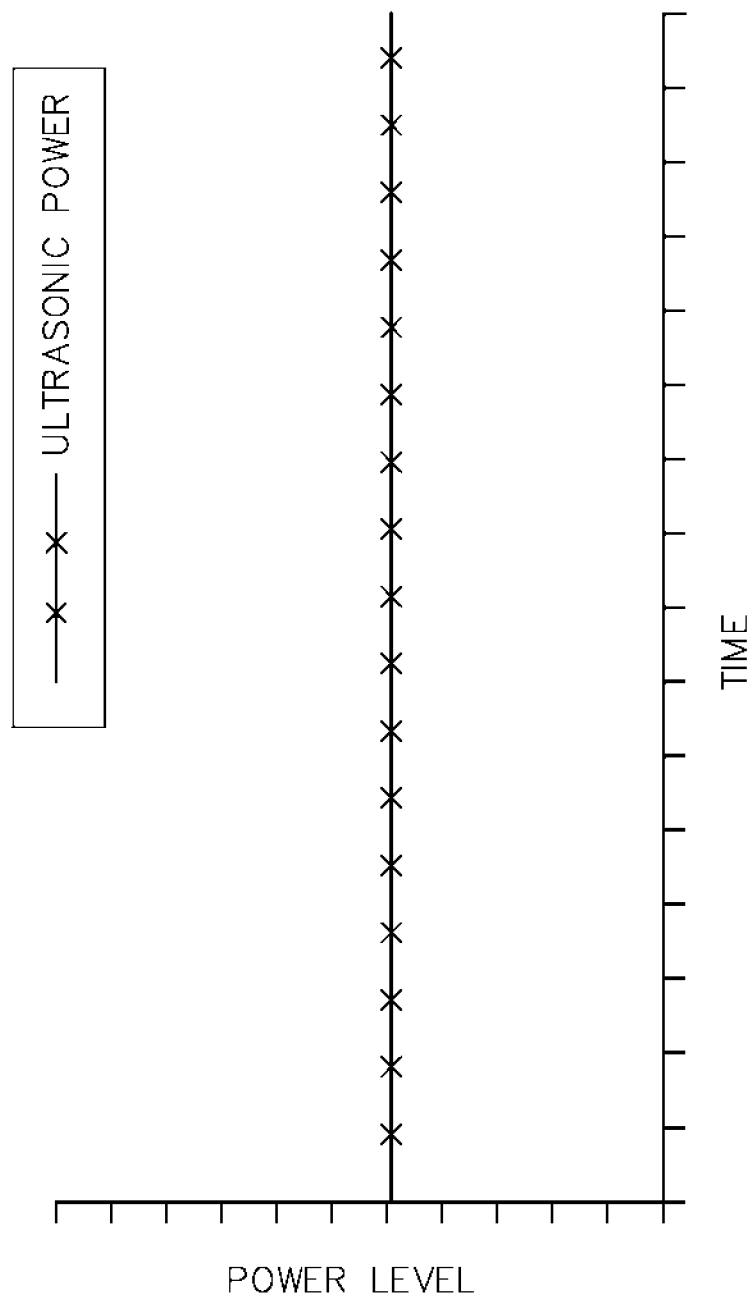

ULTRASONIC SURGICAL INSTRUMENT WITH ELECTROSURGICAL FEATURE

This application is a continuation of U.S. patent application Ser. No. 14/086,085, entitled "Ultrasonic Surgical Instrument with Electrosurgical Feature," filed Nov. 21, 2013, and issued as U.S. Pat. No. 9,949,785 on Apr. 24, 2018.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, now abandoned, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015 the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now abandoned, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, know expired), entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," issued as U.S. Pat. No. 9,393,037 on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a schematic view of another exemplary power operation of the instrument of FIG. 2.

Figure 1:
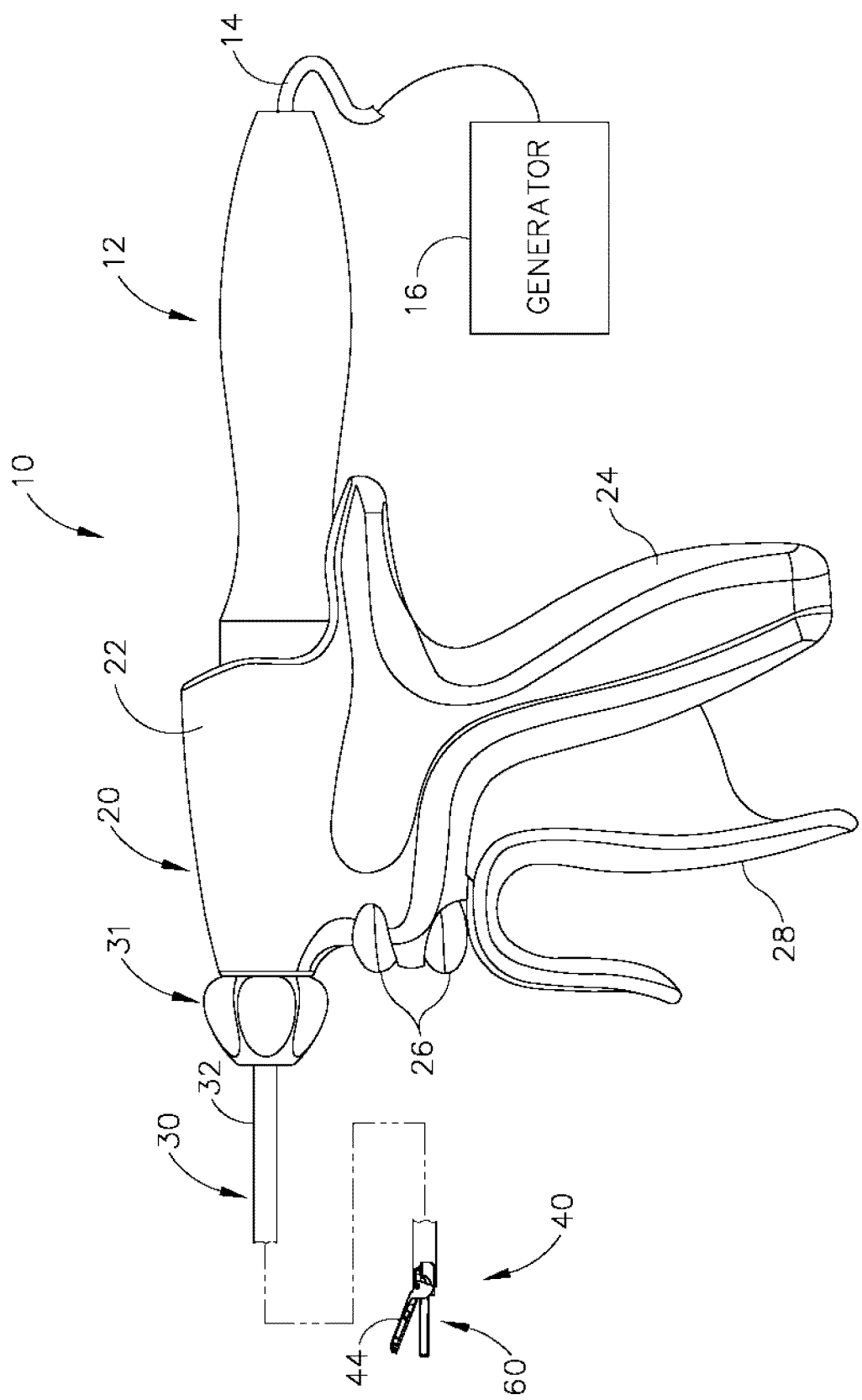
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874 (now abandoned); U.S. Pub. No. 2007/0191713 (now abandoned); U.S. Pub. No. 2007/0282333 now abandoned); U.S. Pub. No. 2008/0200940 now abandoned); U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; U.S. patent application Ser. No. 13/657,553 issued as U.S. Pat. No. 9,095,367 on Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (60) and a pivoting clamp arm (44). Clamp arm (44) is coupled with trigger (28) such that clamp arm (44) is pivotable toward ultrasonic blade (60) in response to pivoting of trigger (28) toward pistol grip (24); and such that clamp arm (44) is pivotable away from ultrasonic blade (60) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

End effector (40) of the present example comprises clamp arm (44) and ultrasonic blade (60). Clamp arm (44) includes a clamp pad that is secured to the underside of clamp arm (44), facing blade (60). Clamp arm (44) is operable to selectively pivot toward and away from blade (60) to selectively clamp tissue between clamp arm (44) and blade (60) in response to pivoting of trigger (28) toward pistol grip (24). Blade (60) of the present example is operable to vibrate at ultrasonic frequencies in order to effectively cut through and seal tissue, particularly when the tissue is being clamped between clamp arm (44) and blade (60). Blade (60) is positioned at the distal end of an acoustic drivetrain that includes transducer assembly (12) to vibrate blade (60). By way of example only, the acoustic drivetrain may be configured in accordance with various teachings of various references that are cited herein.

In the present example, the distal end of blade (60) is located at a position corresponding to an anti-node associated with resonant ultrasonic vibrations communicated through a flexible acoustic waveguide, in order to tune the acoustic assembly to a preferred resonant frequency $f_o$ when the acoustic assembly is not loaded by tissue. When transducer assembly (12) is energized, the distal end of blade (60) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguides to reach blade (60), thereby providing oscillation of blade (60) at the resonant ultrasonic frequency. Thus, when tissue is secured between blade (60) and clamp arm (44), the ultrasonic oscillation of blade (60) may simultaneously sever the tissue and denature the proteins in adjacent tissue cells, thereby providing a coagulative effect with relatively little thermal spread. In some versions, an electrical current may also be provided through blade (60) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

II. Exemplary Ultrasonic Surgical Instrument with Integrated RF Energy

In some instances, when instrument (10) is used to cut and seal tissue, some portions of tissue at the surgical site may bleed after end effector (40) is pulled away from the transected/sealed tissue. It may be desirable to provide one or more elements that transmit radio frequency (RF) energy to tissue (e.g., to coagulate or seal the tissue) at end effector (40) to enable the surgeon to "touch up" these bleeding tissue areas by using RF energy to further seal the bleeding tissue in a highly localized fashion. It should be understood that any of the following "bleeder touch up" features may be readily incorporated into end effector (40) of instrument (10). For instance, such features may be integrated directly into one or both of blade (60) and clamp arm (44). Alternatively, such features may be provided as a cartridge, adapter, or other type of retrofit that couples with end effector (40). As yet another merely illustrative alternative, such features may be provided as separate, stand-alone instruments; or may be incorporated into various other kinds of surgical instruments.

An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein. The RF energy delivery capabilities of instrument (10) may be provided in accordance with at least some of the teachings of the above-cited references.

Figure 2:
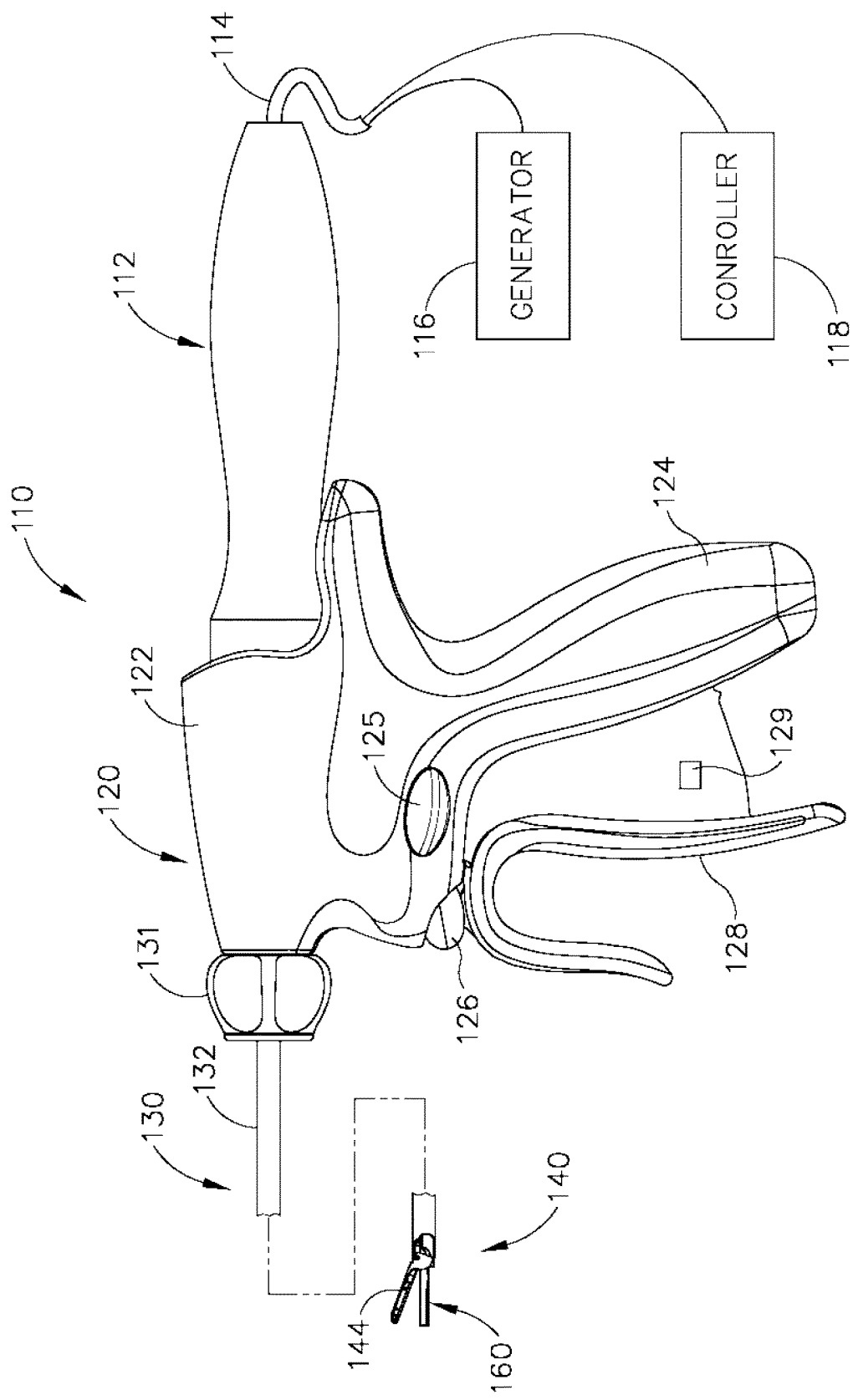
FIG. 2 depicts a side elevational view of another exemplary ultrasonic surgical instrument.

Accordingly, instrument (10) may provide one or more elements that transmit radio frequency (RF) energy to enable the surgeon to "touch up" bleeding tissue areas. For example, FIG. 2 shows an ultrasonic surgical instrument (110) with RF energy capability. Instrument (110) is similar to instrument (10) in that instrument (110) comprises a handle assembly (120), a shaft assembly (130), and an end effector (140). Handle assembly (120) is similar to handle assembly (20) such that handle assembly (120) comprises a body (122) including a pistol grip (124) and a trigger (128) that is pivotable toward and away from pistol grip (124). An ultrasonic transducer assembly (112) extends proximally from body (122) of handle assembly (120). Transducer assembly (112) is coupled with a generator (116) and a controller (118) via a cable (114). Transducer assembly (112) receives electrical power from generator (116) and converts that power into ultrasonic vibrations through piezoelectric principles.

Figure 3:
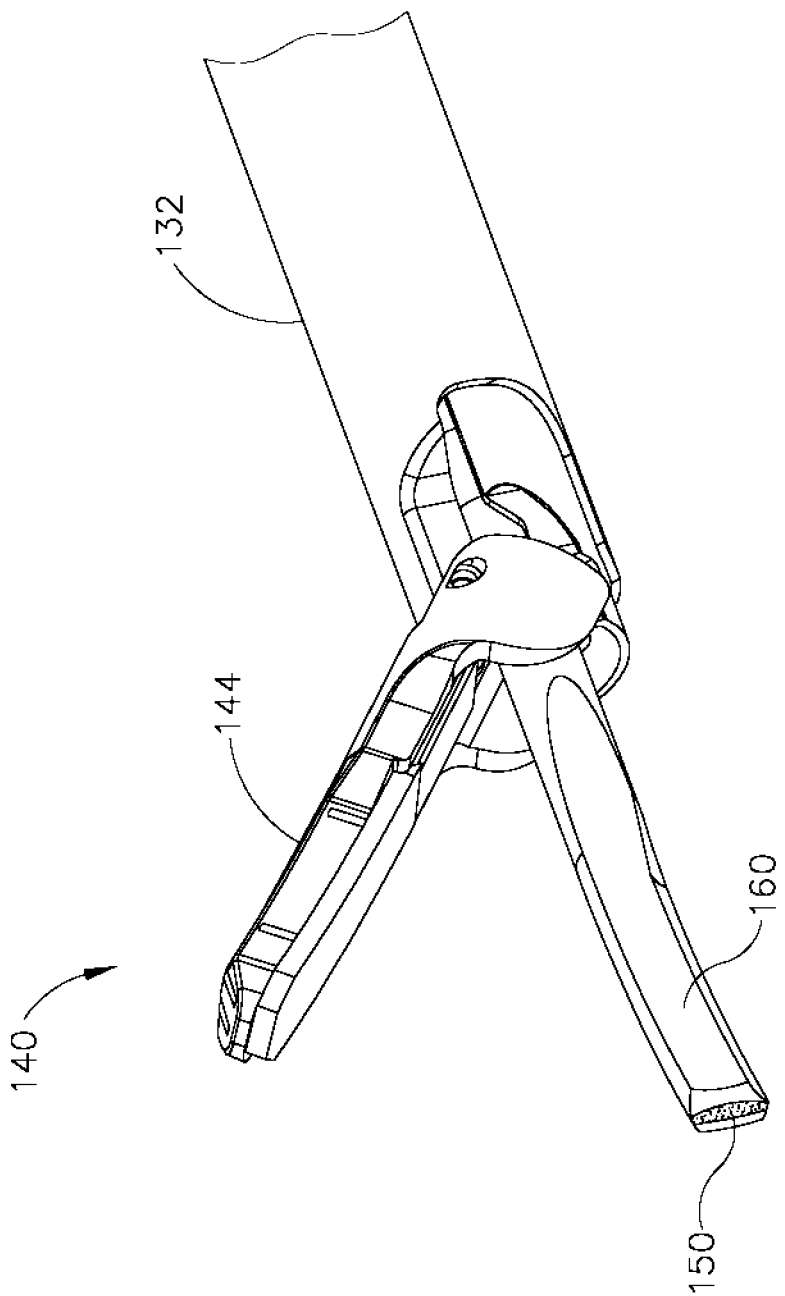
FIG. 3 depicts a partial perspective view of an end effector of the instrument of FIG. 2.

End effector (140) is similar to end effector (40) in that end effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Blade (160) of the present example is operable to vibrate at ultrasonic frequencies in order to effectively cut through and seal tissue, particularly when the tissue is being clamped between clamp arm (144) and blade (160). In the present example, blade (160) is operable to deliver ultrasonic energy in response to actuation of button (126) on handle assembly (120). Blade (160) is further operable to transmit RF energy to tissue. FIG. 3 shows an electrode surface (150) positioned on a distal tip of blade (160). Electrode surface (150) may be formed by masking the distal tip of blade (160) during the coating process of end effector (140) such that the distal tip of blade (160) does not receive a coating, such as polytetrafluoroethylene (PTFE), while the rest of blade (160) receives the coating. While FIG. 3 shows electrode surface (150) positioned on the distal tip of blade (160), electrode surface (150) may be placed on other areas of blade (160) and/or clamp arm (144). Electrode surface (150) is in communication with generator (116) via one or more conductors (not shown) that extend along the length of shaft (130). Alternatively, electrode surface (150) may be in communication with generator (116) by conducting electricity through the body of waveguide (not shown) and blade (160).

Generator (116) is operable to deliver RF energy to electrode surface (150) at an active polarity while the patient may be grounded such that RF current flows from electrode surface (150) to the patient and thereby through tissue positioned adjacent to electrode surface (150). Accordingly, instrument (110) of this example provides monopolar RF energy. To apply such monopolar RF energy, a grounding feature may be needed, such as a ground pad placed under the patient, a ground patch placed on the patient, etc. In the present example, RF energy is transmitted to electrode surface (150) in response to actuation of button (125) on handle assembly (120). In some versions, button (126) is a dedicated ultrasonic button, while button (125) is a dedicated RF button. In some other versions, controller (118) determines whether to apply ultrasonic or RF energy in response to the actuation of button (125) and/or button (126). Examples of such automation are described in greater detail below.

A controller (118) regulates delivery of power from generator (116) to transducer assembly (112) and/or electrode surface (150). FIG. 2 shows controller (118) and generator (116) external to electrosurgical instrument (10), but controller (118) and/or generator (116) may be integral with electrosurgical instrument (110) (e.g., in handpiece (120), etc.), as described in one or more references cited herein or otherwise. Controller (118) may also be integrated into generator (116). It should also be understood that electrode surface (150) may be provided in a variety of alternative locations, configurations, and relationships.

Figure 4:
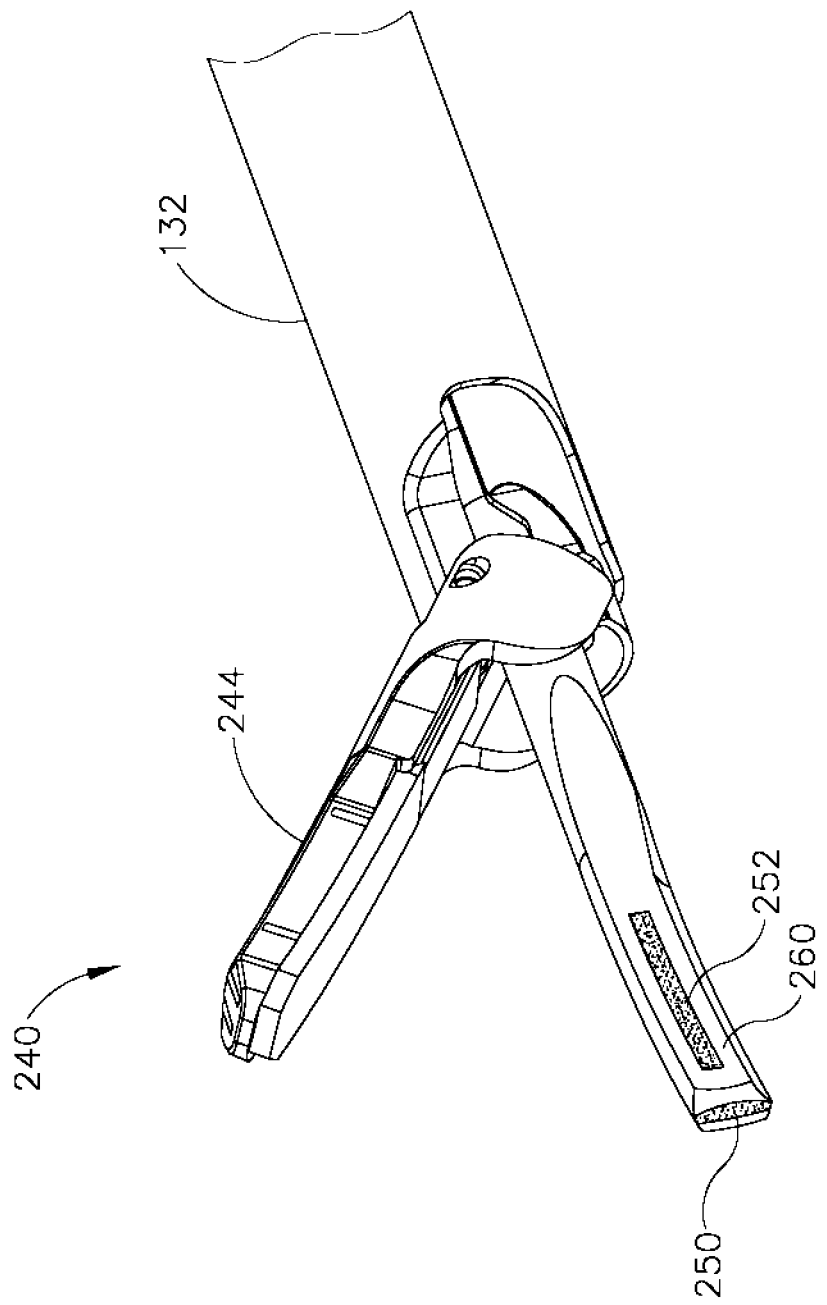
FIG. 4 depicts a partial perspective view of another exemplary end effector for use with the instrument of FIG. 2.
Figure 5:
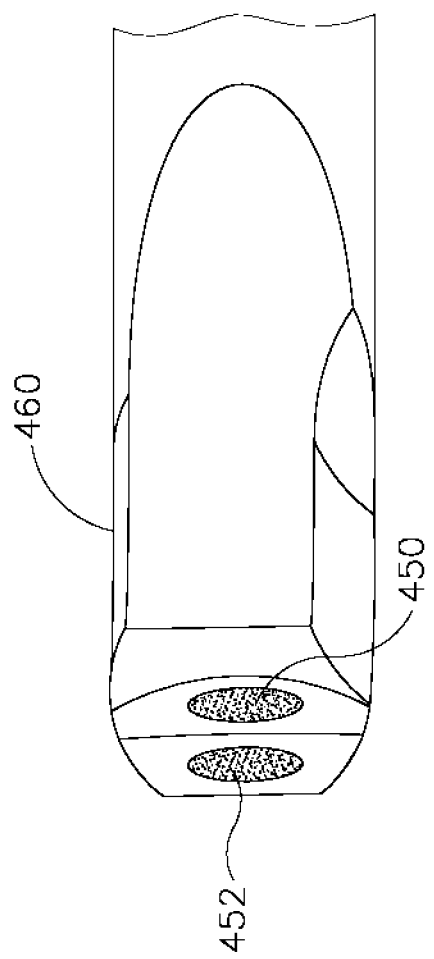
FIG. 5 depicts an end view of another exemplary ultrasonic blade for use with the instrument of FIG. 2.
Figure 6:
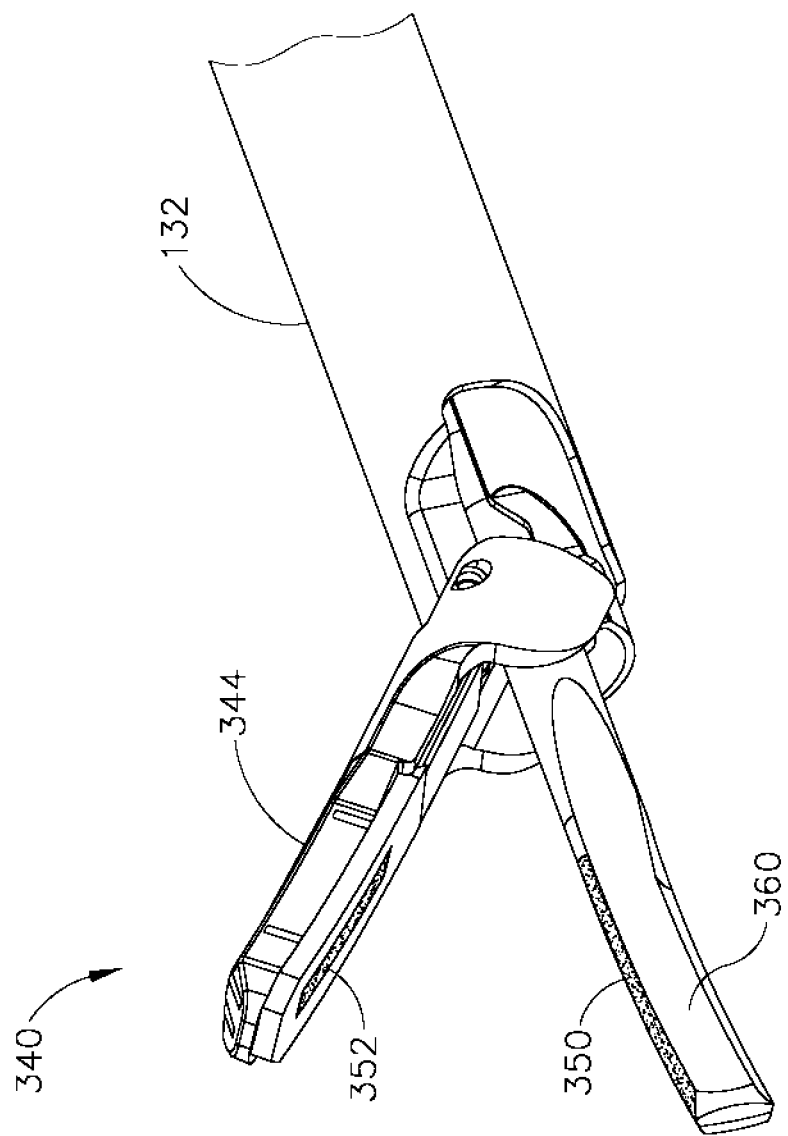
FIG. 6 depicts a partial perspective view of another exemplary end effector for use with the instrument of FIG. 2.

For example, FIG. 4 shows another exemplary end effector (240) that is similar to end effector (140), except that end effector (240) provides bipolar RF energy and comprises a second electrode surface (252) extending along a side portion of blade (160). RF energy is delivered to first electrode surface (250) at an active polarity while second electrode surface (252) serves as a reference/return passive electrode, such that when electrode surfaces (250, 252) are both pressed against tissue, RF current flows between electrode surfaces (250, 252) and thereby through the region of tissue positioned between electrode surfaces (250, 252). It may be necessary in some instances for the surgeon to apply pressure to the tissue with electrode surfaces (250, 252) in order for the tissue to be properly sealed by the bipolar electrode surfaces (250, 252). Of course, electrode surfaces (250, 252) may be positioned at other locations on end effector (240). For example, FIG. 5 shows a distal end of a blade (460) with a pair of electrode surfaces (450, 452) with opposing polarity positioned on the tip of blade (460). Accordingly, the tip of blade (460) is used to seal tissue positioned between electrode surfaces (450, 452). FIG. 6 shows another exemplary end effector (340) that is similar to end effector (240), except that end effector (340) comprises a first electrode surface (350) positioned on a portion of blade (360) facing clamp arm (344) and a second electrode surface (352) positioned on a portion of clamp arm (344) facing blade (360). Accordingly, RF is delivered to end effector (340) to thereby seal tissue positioned between blade (360) and clamp arm (344). Alternatively, both bipolar electrode surfaces (350, 352) may be positioned on clamp arm (344) (e.g. at the distal tip, on the side, etc.). Other suitable electrode configurations will be apparent to one with ordinary skill in the art in view of the teachings herein.

III. Exemplary Automated Energy Delivery

In some versions, it may be desirable to automate the delivery of energy to end effector (40, 140, 240, 340). This may simplify the user interface for instrument (110) to avoid confusion between ultrasonic button (126), RF button (125), and otherwise manually selectable power levels. An automated delivery of energy to end effector (40, 140, 240, 340) may also prevent erroneous use of RF button (125) in an attempt to seal large vessels instead of just using RF button (125) for "touch up" of bleeding tissue areas. Accordingly, button (126) of handle assembly (120) may be designated and used as a "cut" button and button (125) of handle assembly (120) may be designated and used as a "coagulation" button. When buttons (125, 126) are actuated, controller (118) may automatically provide RF and/or ultrasonic power to end effector (40, 140, 240, 340) based on sensed conditions. Those sensed conditions may include (but need not necessarily be limited to) the presence of tissue between clamp arm (144, 244, 344) and blade (160, 260, 360, 460), the position of clamp arm (144, 244, 344) in relation to blade (160, 260, 360, 460), and/or which button (125, 126) is being actuated. The following are merely illustrative examples of providing automated power to blade (160, 260, 360, 460) and/or electrode surfaces (150, 250, 252, 350, 352, 450, 452). Other suitable automated energy configurations will be apparent to one with ordinary skill in the art in view of the teachings herein.

A. Exemplary Automated RF Energy Delivery Based on Completion of Ultrasonic Energy Delivery In some versions, instrument (110) automatically applies RF energy as part of the ultrasonic sequence. For example, controller (118) automatically initiates an RF algorithm near the end of the ultrasonic sequence (i.e. end effector (140) applies RF energy to tissue after blade (160) has applied sufficient ultrasonic energy to the tissue). Controller (118) may detect the end of the ultrasonic sequence by determining a decrease in the amount of tissue load on blade (160, 260, 360, 460) through the frequency at which transducer assembly (112) is vibrating. Alternatively, the end of the ultrasonic sequence may be determined when the user releases ultrasonic button (126). Controller (118) may further sense whether tissue has been transected and fallen away from end effector (40, 140, 240, 340) by initiating a low voltage RF pulse to measure the impedance of tissue at the distal portion of end effector (40, 140, 240, 340). While the term "impedance" is used herein, it should not be read as indicating that the inventors only contemplate the use of alternating current. In some instances, direct current may be used to measure resistance in tissue at the distal portion of end effector (40, 140, 240, 340). Thus, the term "impedance" should be read as implicitly including "resistance." In other words, the term "impedance" as used herein should be read as being synonymous with the term "resistance."

If the impedance level is sufficiently high in the present example, this indicates that there is no tissue present at end effector (40, 140, 240, 340). If the impedance level is sufficiently low, this indicates that there is tissue present at end effector (40, 140, 240, 340). The impedance level may be determined at electrode surfaces (150, 250, 252, 350, 352, 450, 452), which produce a path of least resistance to end effector (40, 140, 240, 340). Sensing the presence of tissue at end effector (40, 140, 240, 340) may prevent overheating of electrode surfaces (150, 250, 252, 350, 352, 450, 452) by sensing tissue absence without needing an ultrasonic frequency change. Other suitable methods for determining the end of the ultrasonic sequence will be apparent to one with ordinary skill in the art in view of the teachings herein.

Once the end of the ultrasonic sequence is detected, controller (118) communicates to generator (116) to thereby provide an RF pulse of energy to the tissue via electrode surfaces (150, 250, 252, 350, 352, 450, 452). This produces a highly localized coagulation feature that is automatically triggered just before the end of the ultrasonic sequence based on tissue presence. The delivery of RF energy is activated before tissue falls away from end effector (40, 140, 240, 340). Although the present example describes delivering RF energy at the end of an ultrasonic sequence, RF energy may also be activated during other portions of a sequence, such as at the beginning and/or periodically throughout the sequence. This may ensure that coagulation is performed before tissue falls away from end effector (40, 140, 240, 340). Of course, in some instances the ultrasonic vibrations of blade (160) may alone provide sufficient coagulation/sealing of the tissue.

In some versions, a low pulse of RF energy is periodically applied to end effector (40, 140, 240, 340) to measure the impedance at the distal portion of end effector (40, 140, 240, 340). This may sense the presence of an iron filled fluid, such as blood. If a bleeder is detected by the presence of a ferrous fluid based on the impedance level at end effector (40, 140, 240, 340), controller (118) may stop activating ultrasonic energy and then apply a cycling RF energy to end effector (40, 140, 240, 340). RF energy may be applied to end effector (40, 140, 240, 340) until there is a lower amount of iron filled fluid, or no iron filled fluid, sensed by instrument (110). This may signify that a bleeder has been sealed, and the ultrasonic transaction could then be reactivated. It should be understood that electrode surfaces (150, 250, 252, 350, 352, 450, 452) may be readily used to sense tissue impedance. For instance, controller (118) may apply a voltage to electrode surfaces (150, 250, 252, 350, 352, 450, 452) and then measure the impedance provided by the tissue, based on the applied voltage. Other suitable structures and techniques that may be used to measure tissue impedance will be apparent to those of ordinary skill in the art in view of the teachings herein.

B. Exemplary Automated Energy Delivery Based on Operating Modes

In other versions, controller (118) of instrument (110) determines the appropriate mode of operation by monitoring a series of conditions to provide automatic energy delivery based on those conditions. For example, controller (118) may monitor whether "cut" button (125) and/or "coagulation" button (126) is actuated on handle assembly (120), whether clamp arm (144, 244, 344) is open or closed, and/or whether tissue is present adjacent to or between blade (160, 260, 360, 460) and clamp arm (144, 244, 344). Of course, any of these conditions may be omitted, substituted, and/or supplemented such that the operating mode of instrument (110) may be determined by a single condition or a combination of other conditions. Other suitable conditions will be apparent to one with ordinary skill in the art in view of the teachings herein.

Referring back to FIG. 2, handle assembly (120) comprises a sensor (129) positioned on trigger (128). Sensor (129) of the present example is in communication with controller (118) and is configured to sense the position of trigger (128) relative to grip (124). By way of example only, sensor (129) may comprise an accelerometer, a strain gauge, a piezoelectric sensor, etc. Accordingly, sensor (129) communicates to controller (118) when trigger (128) is actuated to an open or closed position. Sensor (129) may also sense the clamp force of trigger (128) to assess whether tissue is present at end effector (40, 140, 240, 340). Accordingly, sensor (129) may sense the amount of force being applied to trigger (128) to determine whether tissue is being compressed between clamp arm (44, 144, 244, 344) and blade (60, 160, 260, 360, 460). Although the present example describes sensor (129) positioned on trigger (128), other types of sensors (129) may be used and/or placed at other locations on instrument (110) (e.g., end effector (40, 140, 240, 340), etc.). Suitable alternative sensor configurations will be apparent to one with ordinary skill in the art in view of the teachings herein. By way of example only, the presence of tissue at end effector (40, 140, 240, 340) may be sensed in accordance with at least some of the teachings of U.S. Patent Publication No. 2012/0116379, entitled "Motor Driven Electrosurgical Device With Mechanical and Electrical Feedback," published on May 10, 2012, issued as U.S. Pat. No. 9,161,803 on Oct. 20, 2015, the disclosure of which is incorporated by reference herein. Alternatively, controller (118) may sense the presence of tissue at end effector (40, 140, 240, 340) by initiating a low voltage RF pulse to measure the impedance level at the distal portion of end effector (40, 140, 240, 340), as described above. Other suitable ways in which instrument (110) may sense the presence of tissue at end effector (40, 140, 240, 340) will be apparent to one with ordinary skill in the art in view of the teachings herein.

Based on the described sensed conditions, instrument (110) may then provide automated energy to end effector (40, 140, 240, 340) of instrument (110). Table 1 shows merely illustrative examples of such automated energy delivery to end effector (40, 140, 240, 340) based on whether clamp arm (44, 144, 244, 344) is in an open or closed position relative to blade (60, 160, 260, 360, 460), whether "cut" button (126) or "coagulation" button (125) is activated, and whether tissue is sensed adjacent to end effector (40, 140, 240, 340) or between clamp arm (44, 144, 244, 344) and blade (60, 160, 260, 360, 460). The algorithm shown in Table 1 may be executed by a control logic in controller (118). Various suitable hardware that may be used (e.g., microprocessor, ASIC, printed circuit board, etc.) to store and execute such a control logic will be apparent to those of ordinary skill in the art in view of the teachings herein. Table 1 is shown below.

TABLE 1

| Example | Clamp Arm Position | Button Activated | Tissue Presence between Clamp Arm and Blade Sensed | Perceived Surgical Intent | Energy Delivery |
|---|---|---|---|---|---|
| 1 | Closed | Coagulation button (126) | No | Spot coagulation | RF |
| 2 | Open | Coagulation button (126) | No | Spot coagulation | RF |
| 3 | Open | Coagulation button (126) | Yes | Seal/cut tissue | Either: (i) None, or (ii) Blended RF and Ultrasonic |
| 4 | Closed | Coagulation button (126) | Yes | Seal/cut tissue | Blended RF and Ultrasonic |
| 5 | Open | Cut button (125) | No | Back scoring | Ultrasonic |
| 6 | Closed | Cut button (125) | Yes | Seal/cut tissue | Ultrasonic |
| 7 | Open | Cut button (125) | Yes | Either: (i) Seal/cut tissue with large tissue bite, (ii) back scoring, or (iii) otomy drilling | Ultrasonic |
| 8 | Closed | Cut button (125) | No | Either: (i) Seal/cut tissue with thin or no tissue between clamp arm and blade, (ii) Spot coagulation | Either: (i) Ultrasonic with power reduction, or (ii) RF |

Figure 7:
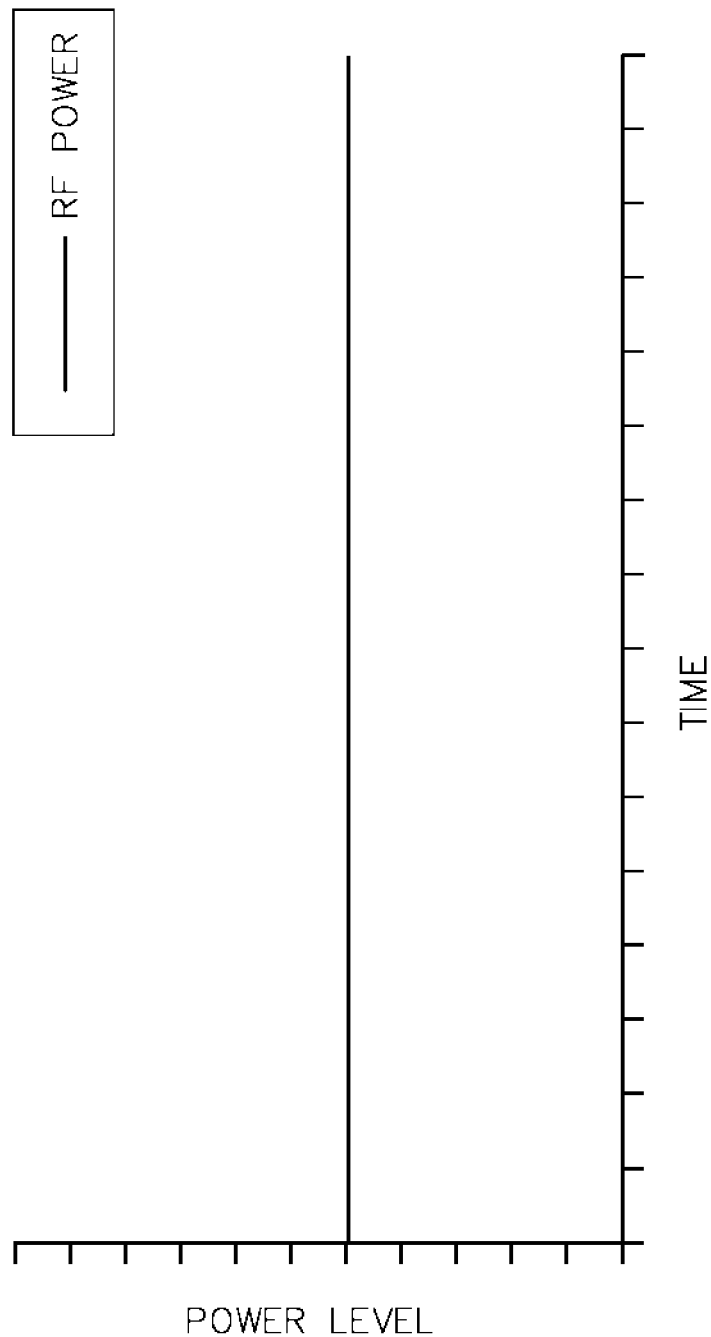
FIG. 7 depicts a schematic view of an exemplary power operation of the instrument of FIG. 2.

In the first example shown in Table 1, clamp arm (44, 144, 244, 344) is closed relative to blade (60, 160, 260, 360, 460), "coagulation" button (125) is activated, and no tissue is detected between clamp arm (44, 144, 244, 344) and blade (60, 160, 260, 360, 460). Based on these conditions, the perceived surgical intent is to perform a spot, or "touch up" coagulation. Controller (118) executes the control algorithm to cause generator (116) to provide RF energy at electrode surfaces (150, 250, 252, 350, 352, 450, 452) of end effector (40, 140, 240, 340). An example of such RF energy delivery is depicted in FIG. 7. Electrode surfaces (150, 250, 252, 350, 352, 450, 452) thereby perform a spot, or "touch up" coagulation to tissue positioned adjacent to (in monopolar versions) or between (in bipolar versions) electrode surfaces (150, 250, 252, 350, 352, 450, 452). While FIG. 7 shows a continuous amount of RF power being applied through instrument (110), the level of RF power may be increased/decreased throughout the sequence, or the RF power may be pulsed during the sequence. Other suitable RF power configurations will be apparent to one with ordinary skill in the art in view of the teachings herein.

In the second example depicted in Table 1, clamp arm (44, 144, 244, 344) is open relative to blade (60, 160, 260, 360, 460), "coagulation" button (125) is activated, and no tissue is detected between clamp arm (44, 144, 244, 344) and blade (60, 160, 260, 360, 460). Based on these conditions, the perceived surgical intent is to perform a spot, or "touch up" coagulation. Controller (118) executes the control algorithm to cause generator (116) to provide RF energy at electrode surfaces (150, 250, 252, 350, 352, 450, 452) of end effector (40, 140, 240, 340), as shown in FIG. 7. Electrode surfaces (150, 250, 252, 350, 352, 450, 452) thereby perform a spot, or "touch up" coagulation to tissue positioned adjacent to (in monopolar versions) or between (in bipolar versions) electrode surfaces (150, 250, 252, 350, 352, 450, 452). While FIG. 7 shows a continuous amount of RF power being applied through instrument (110), the level of RF power may be increased/decreased throughout the sequence, or the RF power may be pulsed during the sequence. Other suitable RF power configurations will be apparent to one with ordinary skill in the art in view of the teachings herein.

The third example in Table 1 depicts clamp arm (44, 144, 244, 344) open relative to blade (60, 160, 260, 360, 460), "coagulation" button (125) activated, and tissue present between clamp arm (44, 144, 244, 344) and blade (60, 160, 260, 360, 460). Based on these conditions, the perceived surgical intent is to seal and/or cut the tissue with end effector (40, 140, 240, 340). In some versions, to prevent inadvertent activation of electrode surfaces (150, 250, 252, 350, 352, 450, 452) and blade (60, 160, 260, 360, 460) with clamp arm (44, 144, 244, 344) open relative to blade (60, 160, 260, 360, 460) under these conditions, controller (118) prevents generator (116) from providing energy at end effector (40, 140, 240, 340). Controller (118) may prompt the user to maintain full clamp arm (44, 144, 244, 344) closure to apply energy to end effector (40, 140, 240, 340). In addition or in the alternative, controller (118) may prompt the user to release button (125) and press button (126) instead.

As yet another merely illustrative alternative, in response to the conditions noted above in the third example, controller (118) may execute a control algorithm to cause generator (116) to provide a blend of RF energy and ultrasonic energy at end effector (40, 140, 240, 340). Examples of such blended energy are shown in FIGS. 8-11.

Figure 8:
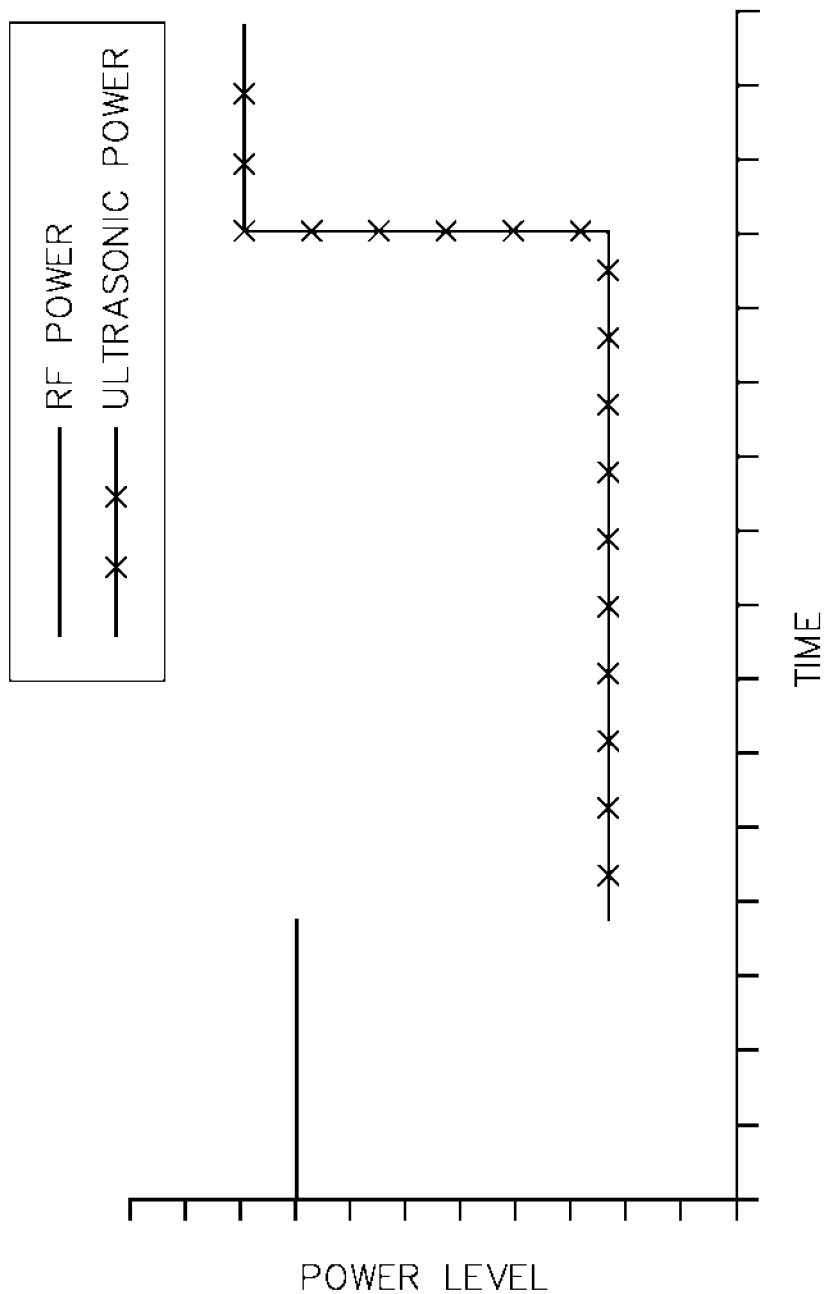
FIG. 8 depicts a schematic view of another exemplary power operation of the instrument of FIG. 2.

FIG. 8 shows continuous RF power being applied for a first duration/period of time. After that first period of time expires, generator (116) drives blade (60, 160, 260, 360, 460) to apply ultrasonic energy at a low power level for a second duration/period of time. After that second period of time expires, generator (116) drives blade (60, 160, 260, 360, 460) to apply ultrasonic energy at a high power level for a third duration/period of time.

Figure 9:
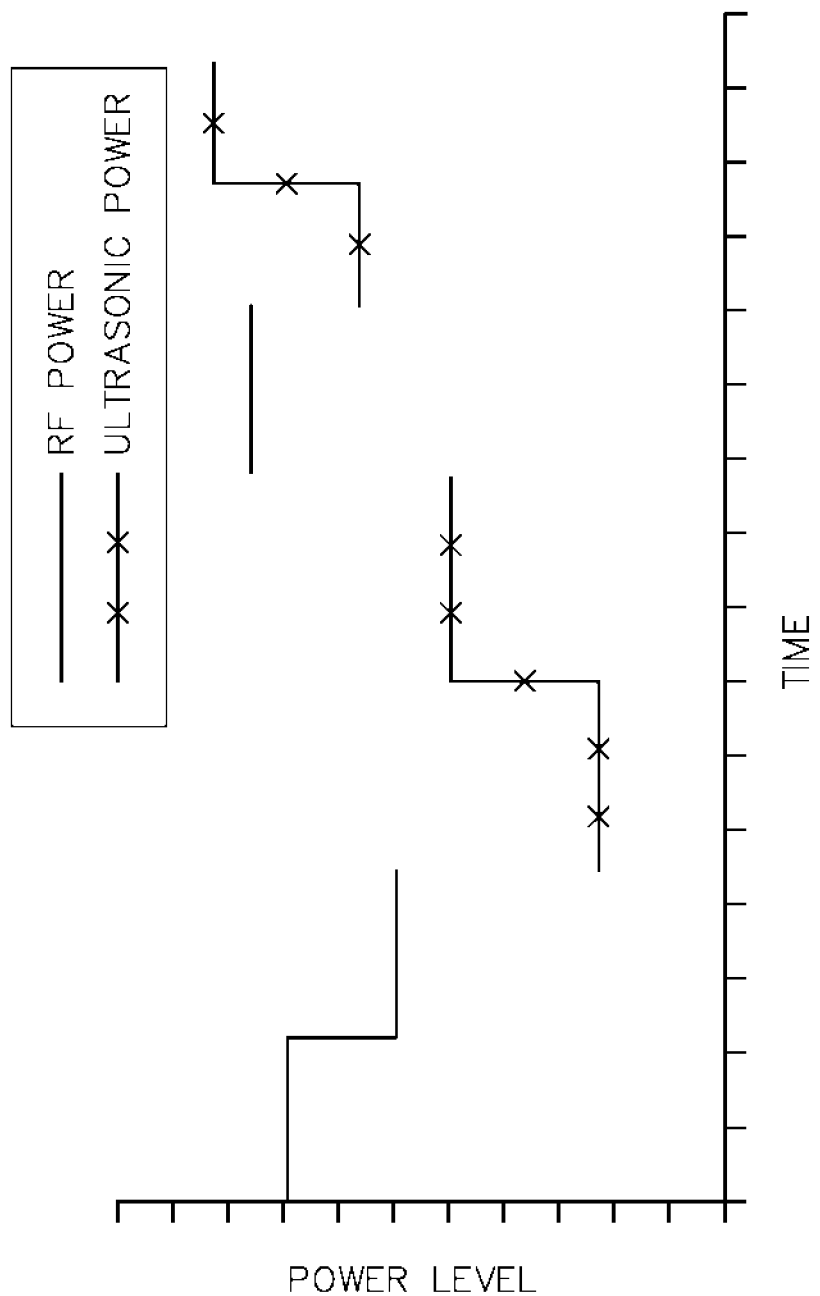
FIG. 9 depicts a schematic view of another exemplary power operation of the instrument of FIG. 2.

Alternatively, generator (116) may alternate between RF power and ultrasonic power. For example, FIG. 9 shows RF power being applied for a first duration/period of time. After that first period of time expires, generator steps down the RF power level to apply lower power RF energy at end effector (40, 140, 240, 340) for a second duration/period of time. After that second period of time expires, generator (116) drives blade (60, 160, 260, 360, 460) to apply ultrasonic energy at a low power level for a third duration/period of time. After that third period of time expires, generator (116) steps up the ultrasonic power level to apply a higher level of ultrasonic energy at blade (60, 160, 260, 360, 460) for a fourth duration/period of time. After that fourth period of time expires, generator (116) applies a high level of RF energy at end effector (40, 140, 240, 340) for a fifth duration/period of time. After that fifth period of time expires, generator (116) drives blade (60, 160, 260, 360, 460) to apply ultrasonic energy at a high power level for a sixth duration/period of time. After that sixth period of time expires, generator (116) increases the ultrasonic power level to drive blade (60, 160, 260, 360, 460) at a higher level of ultrasonic energy for a seventh duration/period of time.

Figure 10:
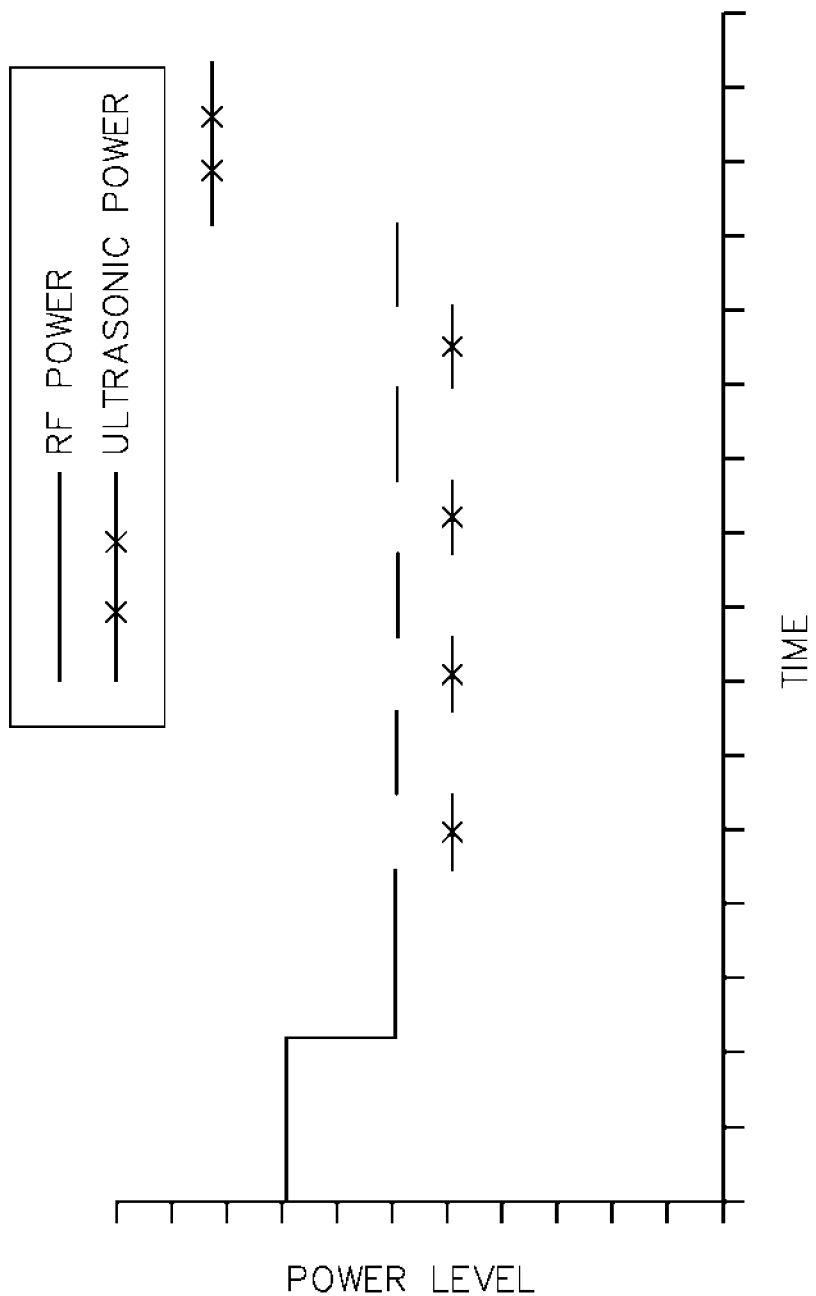
FIG. 10 depicts a schematic view of another exemplary power operation of the instrument of FIG. 2.

FIG. 10 shows another example of blended RF and ultrasonic power that pulses between RF and ultrasonic power. In FIG. 10, RF power is applied for a first duration/period of time. After that first period of time expires, generator (116) decreases the RF energy being applied to apply a lower level of RF energy at end effector (40, 140, 240, 340) for a second duration/period of time. After that second period of time expires, generator (116) drives blade (60, 160, 260, 360, 460) to apply a low level of ultrasonic energy for a third duration/period of time. After that third period of time expires, generator (116) applies the lower level of RF energy to end effector (40, 140, 240, 340) for a fourth duration/period of time. Generator (116) may alternate between the ultrasonic energy and RF energy any suitable number of times. In this example, generator (116) only applies ultrasonic energy or RF energy at any given moment, such that ultrasonic energy and RF energy are not applied simultaneously. In some other versions, however, ultrasonic energy and RF energy may be applied simultaneously. In the present example, after the alternating power sequence is complete, generator (116) drives blade (60, 160, 260, 360, 460) to apply ultrasonic energy at a high power level for an additional duration/period of time.

Figure 11:
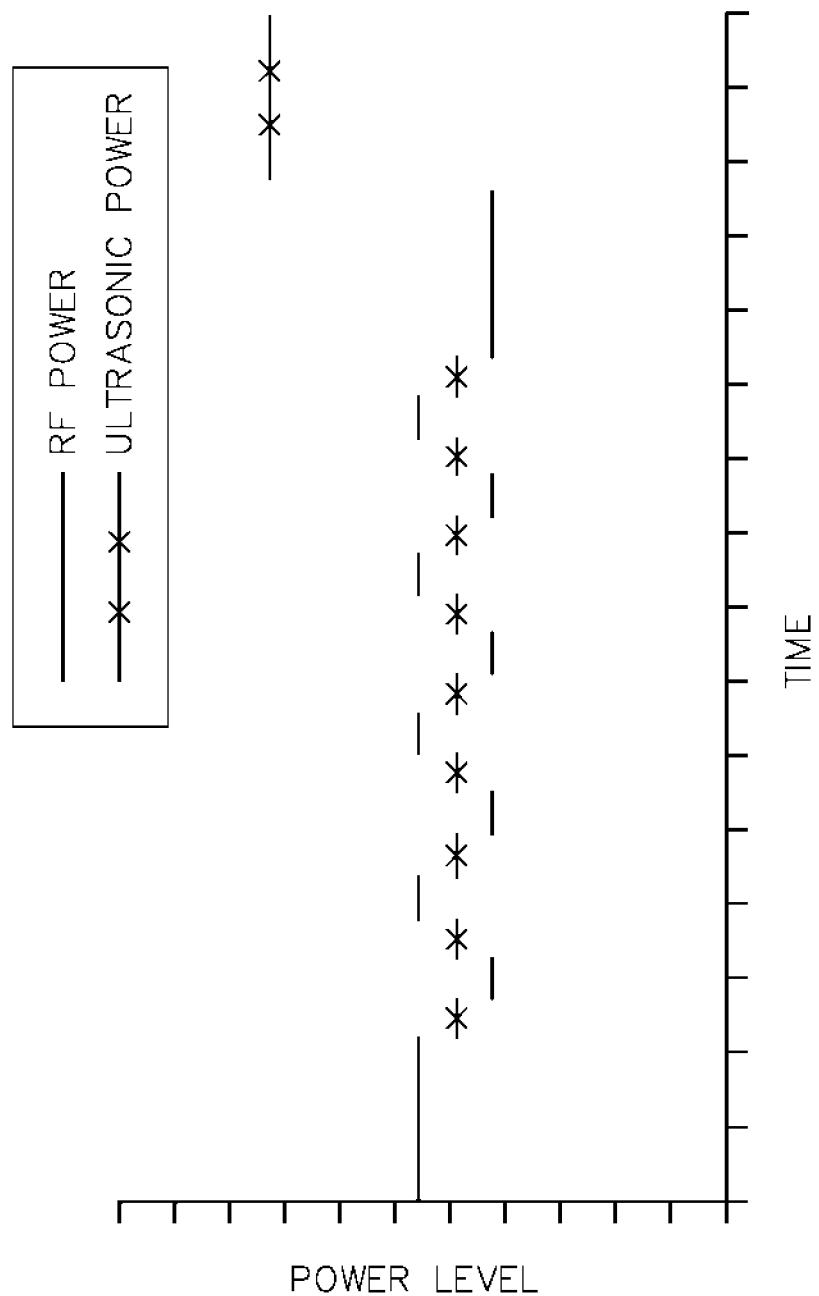
FIG. 11 depicts a schematic view of another exemplary power operation of the instrument of FIG. 2.

In the exemplary control algorithm shown in FIG. 11, a generator provides a continuous amount of RF power for a first duration/period of time. After that first period of time expires, generator (116) drives blade (60, 160, 260, 360, 460) to apply a low power level of ultrasonic energy for a second duration/period of time. After that second period of time expires, generator (116) applies a low level of RF energy for a third duration/period of time. After that third period of time expires, generator (116) drives blade (60, 160, 260, 360, 460) to apply the low level of ultrasonic energy for a fourth duration/period of time. After that fourth period of time expires, generator (116) applies a high level of RF energy for a duration/period of time. Generator (116) may alternate between the high level of RF energy, the low level of ultrasonic energy, and the low level of RF energy any suitable amount of times. Generator (116) then drives blade (60, 160, 260, 360, 460) to apply a high level of ultrasonic energy for an additional duration/period of time.

Of course, these are merely illustrative examples of blended RF and ultrasonic power configurations and other suitable configurations will be apparent to one with ordinary skill in the art in view of the teachings herein. For example, generator (116) may simultaneously apply RF and ultrasonic power to instrument (110); or the increase and/or decrease in power may be ramped instead of stepped. In any case, blended application of RF and ultrasonic power may ultimately cut and seal tissue positioned between end effector (40, 140, 240, 340).

In the fourth example depicted in Table 1, clamp arm (44, 144, 244, 344) is closed relative to blade (60, 160, 260, 360, 460), "coagulation" button (125) is activated, and tissue is detected at end effector (40, 140, 240, 340). Based on these conditions, the perceived surgical intent is to seal and/or cut tissue with end effector (40, 140, 240, 340). Controller (118) automatically communicates to generator (116) to provide a blend of RF energy and ultrasonic energy at end effector (40, 140, 240, 340). Such a blend may be provided in accordance with the examples shown in FIGS. 8-11 and described above. Alternatively, the blend of RF energy and ultrasonic energy may be provided in any other suitable fashion.

In the fifth example depicted in Table 1, clamp arm (44, 144, 244, 344) is open relative to blade (60, 160, 260, 360, 460), "cut" button (126) is activated, and no tissue is detected between clamp arm (44, 144, 244, 344) and blade (60, 160, 260, 360, 460). Based on these conditions, the perceived surgical intent is to back score tissue with blade (60, 160, 260, 360, 460). Controller (118) executes a control algorithm to cause generator (116) to provide ultrasonic energy to end effector (40, 140, 240, 340), as shown in FIG. 12. While FIG. 12 shows a continuous amount of ultrasonic power being applied to instrument (110), the level of ultrasonic power may be increased/decreased throughout the sequence, or the ultrasonic power may be pulsed during the sequence. Other suitable ultrasonic power configurations will be apparent to one with ordinary skill in the art in view of the teachings herein. Accordingly, a high or maximum level of ultrasonic power may be delivered to blade (60, 160, 260, 360, 460) of end effector (40, 140, 240, 340) to back score the tissue. This may provide for faster cutting of more avascular tissue.

In the sixth example depicted in Table 1, clamp arm (44, 144, 244, 344) is closed relative to blade (60, 160, 260, 360, 460), "cut" button (126) is activated, and tissue is detected between clamp arm (44, 144, 244, 344) and blade (60, 160, 260, 360, 460). Based on these conditions, the perceived surgical intent is to seal and cut tissue with end effector (40, 140, 240, 340). Controller (118) executes the control algorithm to cause generator (116) to provide ultrasonic energy to end effector (40, 140, 240, 340), as shown in FIG. 12. Accordingly, a higher amount of ultrasonic power may be delivered to blade (60, 160, 260, 360, 460) of end effector (40, 140, 240, 340) to seal and cut the tissue. While FIG. 12 shows a continuous amount of ultrasonic power being applied to instrument (110), the level of ultrasonic power may be increased/decreased throughout the sequence, or the ultrasonic power may be pulsed during the sequence. Other suitable ultrasonic power configurations will be apparent to one with ordinary skill in the art in view of the teachings herein.

In the seventh example depicted in Table 1, clamp arm (44, 144, 244, 344) is open relative to blade (60, 160, 260, 360, 460), "cut" button (126) is activated, and no tissue is detected between clamp arm (44, 144, 244, 344) and blade (60, 160, 260, 360, 460). Based on these conditions, the perceived surgical intent is to either (i) seal/cut tissue with a large tissue bite; (ii) back score tissue with blade (60, 160, 260, 360, 460); or (iii) drill anotomy in tissue with blade (60, 160, 260, 360, 460). Controller (118) executes the control algorithm to cause generator (116) to provide ultrasonic energy to end effector (40, 140, 240, 340), as shown in FIG. 12. Accordingly, a higher amount of ultrasonic power may be delivered to blade (60, 160, 260, 360, 460) of end effector (40, 140, 240, 340) to seal and cut the tissue. While FIG. 12 shows a continuous amount of ultrasonic power being applied to instrument (110), the level of ultrasonic power may be increased/decreased throughout the sequence, or the ultrasonic power may be pulsed during the sequence. Other suitable ultrasonic power configurations will be apparent to one with ordinary skill in the art in view of the teachings herein.

In the eighth example depicted in Table 1, clamp arm (44, 144, 244, 344) is closed relative to blade (60, 160, 260, 360, 460), "cut" button (126) is activated, and no tissue is detected between clamp arm (44, 144, 244, 344) and blade (60, 160, 260, 360, 460). Based on these conditions, the perceived surgical intent is to either (i) seal/cut tissue with either a very thin amount of tissue or no tissue positioned between clamp arm (44, 144, 244, 344) and blade (60, 160, 260, 360, 460); or (ii) perform a spot, or "touch up" coagulation with blade (60, 160, 260, 360, 460). In some versions, this causes controller (118) to execute a control algorithm to cause generator (116) to provide ultrasonic energy to end effector (40, 140, 240, 340). In some such versions, the level of ultrasonic power is lower under these conditions than it is in the scenario shown in FIG. 12 and described above (under other conditions). It should also be understood that the level of ultrasonic power may be increased/decreased throughout the sequence, or the ultrasonic power may be pulsed during the sequence. Other suitable ultrasonic power configurations will be apparent to one with ordinary skill in the art in view of the teachings herein.

In some other versions, in response to the conditions noted above in the eighth example, controller (118) may execute a control algorithm to cause generator (116) to provide RF energy at electrode surfaces (150, 250, 252, 350, 352, 450, 452) of end effector (40, 140, 240, 340). An example of such RF energy delivery is depicted in FIG. 7. Electrode surfaces (150, 250, 252, 350, 352, 450, 452) thereby perform a spot, or "touch up" coagulation to tissue positioned adjacent to (in monopolar versions) or between (in bipolar versions) electrode surfaces (150, 250, 252, 350, 352, 450, 452). While FIG. 7 shows a continuous amount of RF power being applied through instrument (110), the level of RF power may be increased/decreased throughout the sequence, or the RF power may be pulsed during the sequence. Other suitable RF power configurations will be apparent to one with ordinary skill in the art in view of the teachings herein.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of treating tissue with a surgical system, wherein the surgical system comprises a surgical instrument having an end effector that includes an ultrasonic blade, a clamp arm, a controller, and at least one electrode, the method comprising:
   (a) capturing tissue between the clamp arm and the ultrasonic blade;
   (b) activating the ultrasonic blade with ultrasonic energy sufficient to cut the captured tissue;
   (c) activating the at least one electrode with RF energy sufficient to seal the captured tissue; and
   (d) automatically determining with the controller to activate the ultrasonic blade or the at least one electrode in response to sensing a presence of tissue at the end effector, wherein sensing a presence of tissue at the end effector comprises measuring an impedance level at the at least one electrode.

2. The method of claim 1, wherein the at least one electrode comprises a first electrode and a second electrode, wherein activating the at least one electrode with RF energy comprises activating the first and second electrodes with bipolar RF energy.

3. The method of claim 2, wherein the first electrode is provided by the ultrasonic blade and the second electrode is provided by the clamp arm.

4. The method of claim 1, wherein the surgical instrument further comprises a first actuator and a second actuator, wherein the method further comprises:
   (a) activating the ultrasonic blade with ultrasonic energy in response to actuation of the first actuator; and
   (b) activating the at least one electrode with RF energy in response to actuation of the second actuator.

5. The method of claim 1, wherein the surgical instrument further comprises at least one actuator, wherein the automatic determination is made by the controller in response to actuation of the at least one actuator.

6. The method of claim 5, wherein the at least one actuator comprises a first actuator and a second actuator, wherein the automatic determination is made by the controller in response to actuation of at least one of the first actuator or the second actuator.

7. The method of claim 1, wherein the automatic determination is made by the controller based on sensing at least one of:
   (i) a presence of tissue at the end effector,
   (ii) a position of the clamp arm relative to the ultrasonic blade, or
   (iii) actuation of an actuator of the surgical instrument.

8. The method of claim 7, wherein the surgical instrument further comprises a trigger operable to actuate the clamp arm, wherein the automatic determination is made by the controller in response to sensing a presence of tissue at the end effector, wherein sensing a presence of tissue at the end effector comprises measuring a force exerted on the trigger by a user.

9. The method of claim 7, wherein the automatic determination is made by the controller based on sensing actuation of an actuator of the surgical instrument and sensing at least one of:
   (i) a presence of tissue at the end effector, or
   (ii) a position of the clamp arm relative to the ultrasonic blade.

10. The method of claim 1, wherein the automatic determination made by the controller comprises one of:
    (i) activating the ultrasonic blade with continuous or pulsed ultrasonic energy, or
    (ii) activating the at least one electrode with continuous or pulsed RF energy.

11. The method of claim 1, wherein the automatic determination made by the controller comprises:
    (i) for a first period, activating the at least one electrode with RF energy,
    (ii) for a second period, activating the ultrasonic blade with a first level of ultrasonic energy, and
    (iii) for a third period, activating the ultrasonic blade with a second level of ultrasonic energy.

12. The method of claim 1, wherein the automatic determination made by the controller comprises activating the at least one electrode with RF energy and activating the ultrasonic blade with ultrasonic energy in an alternating manner.

13. The method of claim 1, wherein the automatic determination made by the controller comprises:
    (i) for a first period, activating the at least one electrode with a first level of RF energy,
    (ii) for a second period, activating the ultrasonic blade with ultrasonic energy, and
    (iii) for a third period, activating the at least one electrode with a second level of RF energy.

14. A method of treating tissue with a surgical system, wherein the surgical system comprises a surgical instrument having an actuator and an end effector that includes an ultrasonic blade, a clamp arm, and an electrode, the method comprising:
    (a) capturing tissue between the clamp arm and the ultrasonic blade;
    (b) sensing a condition at the end effector; and
    (c) in response to actuation of the actuator and based on the sensed condition, automatically activating the ultrasonic blade with ultrasonic energy sufficient to cut the captured tissue and activating the electrode with RF energy sufficient to seal the captured tissue.

15. The method of claim 14, wherein sensing a condition at the end effector comprises sensing at least one of:
    (i) a presence of tissue at the end effector, or
    (ii) a position of the clamp arm relative to the ultrasonic blade.

16. The method of claim 14, wherein automatically activating at least one of the ultrasonic blade or the electrode comprises activating the ultrasonic blade with ultrasonic energy sufficient to cut the captured tissue followed by activating the electrode with RF energy sufficient to seal the captured tissue.

17. A method of treating tissue with a surgical system, wherein the surgical system comprises a surgical instrument having an actuator and an end effector that includes an ultrasonic blade, a clamp arm, and an electrode, the method comprising:
- (a) capturing tissue between the clamp arm and the ultrasonic blade;
- (b) activating the ultrasonic blade with ultrasonic energy sufficient to cut the tissue;
- (c) measuring an impedance level of the tissue at the electrode; and
- (d) based on the measured impedance level, automatically:
  - (i) ceasing activation of the ultrasonic blade with ultrasonic energy, and
  - (ii) activating the electrode with RF energy sufficient to seal the tissue.

18. The method of claim 17, wherein the electrode comprises a first electrode, wherein the end effector further comprises a second electrode, wherein activating the electrode with RF energy sufficient to seal the tissue comprises activating the first and second electrodes with bipolar RF energy.

\* \* \* \* \*